United States Patent [19]

Giggey et al.

[11] 4,369,880

[45] Jan. 25, 1983

[54] POP-UP ARMED SUTURE

[75] Inventors: Robert W. Giggey, Port Washington; Bernard T. Serletic, Manhasset, both of N.Y.; Charles R. Ashley, Clinton, N.J.

[73] Assignee: Howmedica, Inc., New York, N.Y.

[21] Appl. No.: 241,094

[22] Filed: Mar. 6, 1981

[51] Int. Cl.³ .................. A61B 17/04; B65D 85/24
[52] U.S. Cl. .................................. 206/63.3; 206/380
[58] Field of Search .................... 206/63.3, 382, 383, 206/370, 363, 365, 388, 484, 227

[56] References Cited

U.S. PATENT DOCUMENTS

| | | | |
|---|---|---|---|
| 1,387,839 | 8/1921 | Davis | 206/370 |
| 2,587,928 | 3/1952 | Tuck et al. | 206/484 |
| 3,136,418 | 6/1964 | Stacy et al. | 206/63.3 |
| 3,280,971 | 10/1966 | Regan, Jr. | 206/63.3 |
| 3,338,401 | 8/1967 | Regan, Jr. | 206/63.3 |
| 3,363,751 | 1/1968 | Shave et al. | 206/63.3 |
| 3,444,994 | 5/1969 | Kaepernik et al. | 206/63.3 |
| 3,500,998 | 3/1970 | Sanders | 206/382 |
| 3,939,969 | 2/1976 | Miller et al. | 206/63.3 |
| 4,063,638 | 12/1977 | Marwood | 206/63.3 |
| 4,069,912 | 1/1978 | Black et al. | 206/63.3 |
| 4,135,623 | 1/1979 | Thyen | 206/63.3 |

*Primary Examiner*—Joseph Man-Fu Moy
*Assistant Examiner*—Jimmy G. Foster
*Attorney, Agent, or Firm*—Pennie & Edmonds

[57] ABSTRACT

A device for storing and dispensing a suture includes an outer envelope formed of two panel layers which are sealed along their peripheries so as to hermetically enclose a region therebetween. An inner container positioned within the region includes rectangular upper, center and lower panels which are foldably secured along respective score lines. The upper panel has a pocket formed by an overlaying window to snugly retain a needle therein. The upper panel is folded back onto the center panel which receives and retains a major portion of the suture secured to the needle. The lower panel is also folded over the center panel and is coupled to the upper panel. Both the upper and lower panels are capable of slidably moving over the center panel. Interlocking panels secured to lower panel sides lock the upper and lower panels together. Score lines across the upper and lower panels permit the upper and lower panels to interact so that flexing of one panel from a raised configuration to a generally flat configuration causes the other panel to flex from a generally flat configuration to a raised configuration. A window is provided in the upper panel layer and overlies the window of the center panel so that the needle and a portion of the thread are viewable therethrough. After tearing or removing a portion of the upper panel layer so as to expose the window on the center panel, the upper panel layer is depressed adjacent the score line across the lower panel so as to expose a portion of the needle together with a portion of the suture free of the surface of the upper panel. A method for storing and dispensing the suture and respective needle is also disclosed.

42 Claims, 8 Drawing Figures

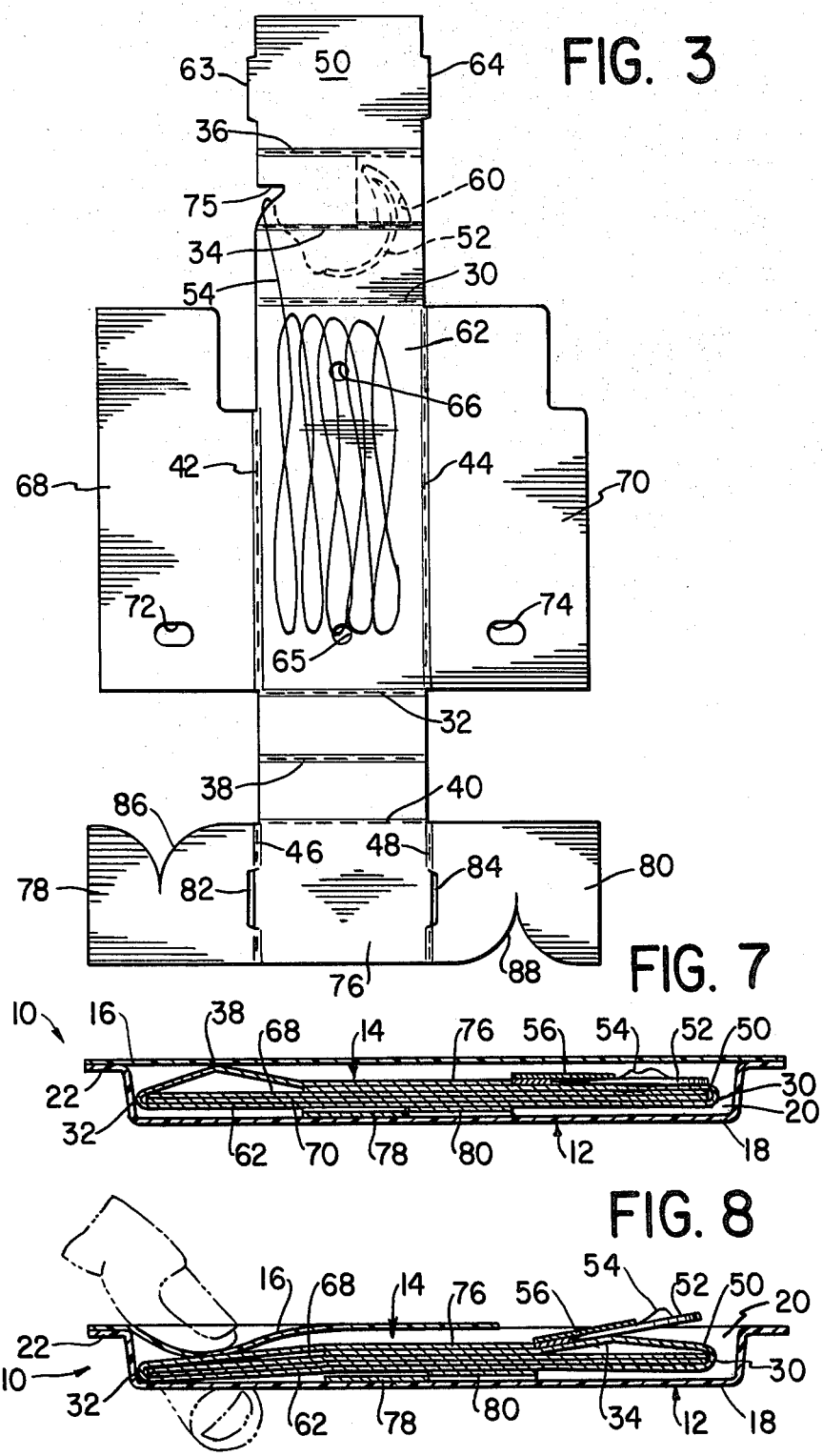

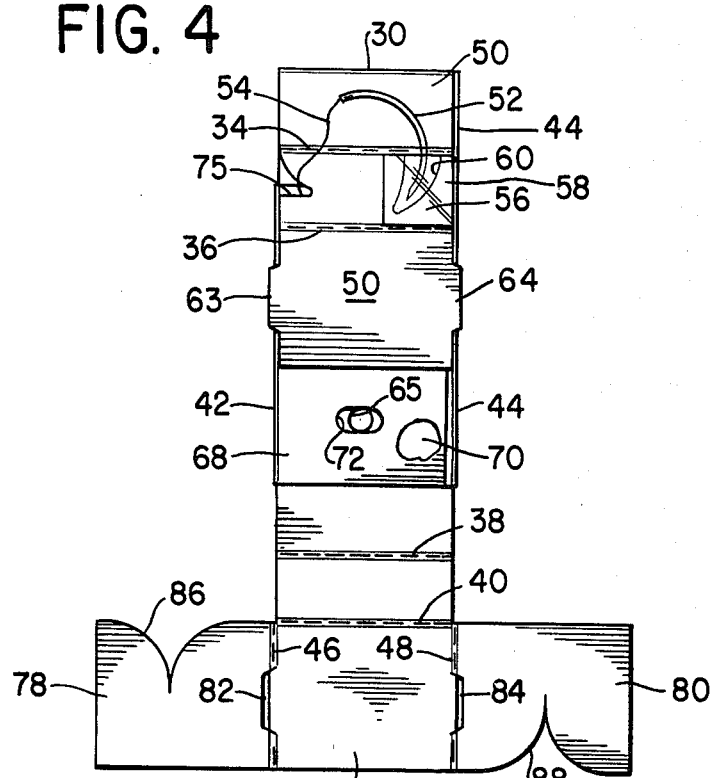
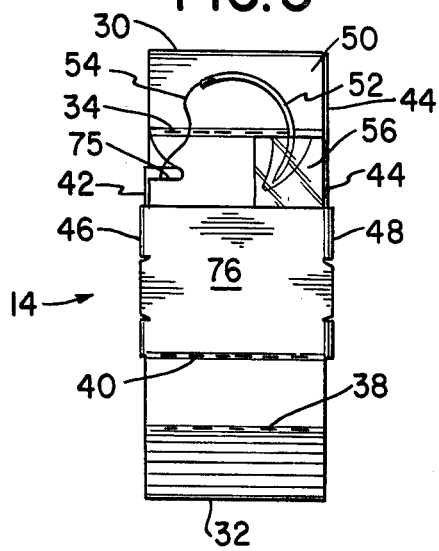
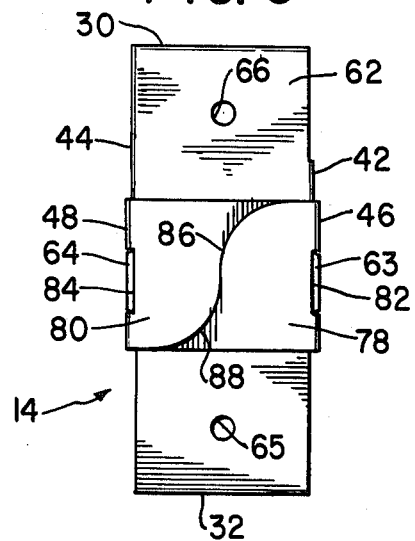

POP-UP ARMED SUTURE

1. TECHNICAL FIELD

The present invention relates to a device for storing a suture prior to its use and, particularly, to a container providing a sterile environment while permitting ease of dispensing the suture when required.

2. BACKGROUND ART

It is well known to employ sutures for the purpose of closing a wound or an incision created during an operation. For this reason, it is necessary that the suture be maintained in a sterile condition at all times prior to its use. Moreover, it is also necessary that the suture be readily available when needed so as to permit efficient and expeditious use thereof.

Typically, sutures are known which are contained in packages so as to preserve the sterile condition of the sutures. Such packages typically provide suitable arrangement of the sutures so as to prevent any entangling of the sutures upon their removal from the package. Such known sutures and their accompanying packages are described in U.S. Pat. Nos. 3,280,971; 3,939,969; 4,063,638; and 4,069,912.

Each of these patents relates to a suture package which contains sutures in a sterile condition prior to use. The U.S. Pat. No. 3,280,971 relates to a suture package intended to retain the suture strands in such a way that they can be removed easily from the package and will not be kinked or bent upon removal. The U.S. Pat. No. 3,280,971 package includes a coiled hollow restraining tube which is retained within a holding sleeve formed from a sterilizable stiff sheet material. The tube is large enough so that a plurality of sutures can be contained therein in a loose fashion and furthermore so that they do not entangle with one another during their storage. Outside of the tube, the sutures at their free end are attached to individual curved needles which are permitted to rest loosely in an unconstrained fashion upon the sheet material.

The U.S. Pat. No. 3,939,969 discloses a suture package including a suture retainer made up of three panels. The suture strand is coiled and placed upon a middle panel while the needle is curved back and superimposed over a second panel which in turn overlies the first panel. Moreover, a third panel thereafter overlies the second panel and thereby covers the needle itself. The third panel itself includes a tab at an end portion which upon being pulled away from the third panel permits separation along a tear line so as to expose the suture needle laying upon the second panel.

The U.S. Pat. No. 4,063,638 relates to a suture package also including an inner envelope consisting of three connected panels. As was the case in the U.S. Pat. No. 3,939,969, the suture strand is placed or retained in a non-entangling configuration upon the second panel which may include strand retainers if desired. One of the end panels along this upper peripheral edge includes a series of perforations and slits extending therefrom to the peripheral edge so as to receive and retain an end portion of the strand. The needle which is attached to the end of the respective strand in turn is placed upon an end panel and is retained thereon by inserting the needle end through a slit provided in the end panel.

Similarly, the U.S. Pat. No. 4,069,912 also relates to a suture package wherein the needle attached to a suture surgical strand is retained underneath an overlapping panel of a suture label by inserting the needle through a slit contained in an overlapping panel portion. Accordingly, only a small portion of the needle is exposed and available for securing with a suitable device for removal of the needle therefrom.

Notwithstanding the improvements which the above-identified patents offer with respect to packages suitable for containing sutures in a sterile condition prior to use, these devices still present difficulties with which the operating personnel must cope.

Most of the presently known suture packages retain the needle portion of the suture in a flat abutting relationship with the packaging material itself. For this reason, removal of the suture is made difficult inasmuch as the needle lies flat against a panel. Typically, a nurse or surgeon is required to dig into the package to get at the needle. This problem is further complicated when dull needle holders are employed. In addition, none of the above-identified suture packages provide for arming from the pack or container either for right or left-handed suturing. Oftentimes, it is necessary for the nurse or surgeon to employ the needle holder as a removal tool since the needle is oftentimes buried in the package and thereafter in a subsequent step to reposition the needle in accordance with the surgeon's needs. For this reason, the suture packages described above do not present an armed suture which is physically convenient and readily viewable prior to use. Also, it is known in typical suture packages that the needle migrates out of its planned or intended location. As a result, the needle may not be found where expected and further searching within the suture package is required. This further complicates the process of removing the needle and suture from the package itself.

Such difficulties also involve the limited visibility which these patented devices provide with respect to the suture and their respective needles. Limited visibility does not permit an easy and efficient determination of the needle count and the product style prior to opening the package itself.

In addition, it is desirable to obtain efficient economy of use which results from not opening the wrong package. Such is the case where the package cover itself totally encloses the inner suture container and for this reason prevents the viewing of the type of suture enclosed. Moreover, it is desirable to permit viewing of the suture while within the container and thereby determine the true characteristics of the suture within without relying upon a two-dimensional description or illustration presented on the package cover.

DISCLOSURE OF THE INVENTION

The present invention relates to a container for dispensing at least one suture secured to one end of a needle, comprising first panel means for retaining a portion of the needle, the first panel means capable of flexing about a first predetermined axis such that the remaining portion of the needle is exposed free of the first panel means upon flexing of the first panel means about the first predetermined axis, second panel means for retaining a major portion of the suture, the second panel means being connected to the first panel means and configured such that the suture can be withdrawn therefrom upon removal of the needle from the first panel means, and third panel means connected to the second panel means and coupled to the first panel means, the third panel means capable of being displaced so as to effect flexing of the first panel means about the first predetermined axis, so as to expose the remaining portion of the needle free of the first panel means.

In a preferred embodiment, the present invention relates to a container for dispensing a suture secured to one end of a needle, comprising first panel means for securely retaining a portion of the needle, the first panel means capable of flexing about a first predetermined axis in the plane of the first panel means such that the remaining portion of the needle is exposed free of the first panel means upon flexing of the first panel means about the first predetermined axis, second panel means for securely retaining a major portion of the suture, the second panel means being connected to the first panel means and configured such that the suture can be withdrawn therefrom upon removal of the needle from the first panel means, and third panel means connected to the second panel means and coupled to the first panel means, the third panel means capable of flexing about a second predetermined axis in the plane of the third panel means such that upon flexing of the third panel means about the second predetermined axis the first panel means is also flexed about the first predetermined axis so as to expose the remaining portion of the needle free of the first panel means. The first panel means includes a window portion permitting viewing of the needle retained in secured relationship with the first panel means. Preferably, the window portion is constructed of transparent material and the first and the second panel means are of a generally rectangular configuration.

The first and second panel means are foldably secured to each other along respective width edges thereof. The width edges are aligned with the first predetermined axis. The container further includes means for enclosing the major portion of the suture retained by the second panel means. According to one embodiment, the suture enclosing means includes a first pair of panels foldably secured to the second panel means along respective longitudinal edges thereof. The first pair of panels are capable of being folded over onto the second panel means such that the major portion of the suture is substantially enclosed. The first panel means is folded over along its longitudinal edge connected to the second panel means so as to slidably overlap a surface portion of the first pair of panels in their folded condition enclosing the major portion of the suture.

Additionally, the third panel means is also of a generally rectangular configuration. The other width edge of the second panel means is foldably secured to a width edge of the third panel means. These width edges are aligned with the second predetermined axis. Means are provided for coupling the first panel means and the third panel means. The coupling means can include a second pair of panels each foldably secured to a respective longitudinal edge of the third panel means. The third panel means can be folded over along its longitudinal edge connected to the second panel means so as to slidably overlap a surface portion of the first pair of panels in their folded condition enclosing the major portion of the suture.

The container further includes an aperture positioned adjacent a longitudinal edge of of the first panel means. The aperture guides the major portion of the suture during its withdrawal from the second panel means. Also, the second panel means includes means for maintaining the major portion of the suture in a predetermined configuration so as to prevent entangling or kinking of the major portion of the suture during dispensing of the suture therefrom.

Preferably, each of the panel means and each of the pairs of panels are integrally constructed of a bleached sulphite board. It is also preferred that each of the panel means and each of the pairs of panels are capable of being sterilized by at least one of irradition and ethylene oxide sterilizing methods.

The present invention also relates to a device for storing and dispensing a suture secured to one end of a needle, comprising outer container means including a first panel layer and a second panel layer of generally like configuration and dimension, the first and second panel layers being secured together along their peripheries so as to define an enclosed region therebetween, said first panel layer including a first window portion permitting viewing of said enclosed region. The device also comprises inner container means positioned within the region which includes first panel means, second panel means and third panel means as described hereinabove. The first panel means includes a second window portion permitting viewing of the needle retained in secured relationship with the first panel means. Preferably, the first window portion is of a larger surface dimension than the second window portion such that the first window portion can overlie the second window portion so as to permit viewing of the entire needle together with at least a portion of the suture through the first and the second window portions. Preferably, the first and the second window portions are constructed of transparent material.

The first panel layer can include a suitably positioned notch so as to permit tearing and removal of the first panel layer adjacent the needle. The first and said second panel layers are each of a generally rectangular configuration and are constructed of a clear polyester capable of being imprinted so as to provide numerical and identifying indicia thereon. If desired, a layer of metallic foil can be superimposed on at least one surface of the second panel layer. Also, the first and the second panel layers are capable of being sterilized by at least one of irradition and ethylene oxide sterilizing methods.

The inner container is of a generally rectangular configuration and is configured and dimensioned so as to be capable of being enclosed within the region defined between the first and the second panel layers.

The present invention also relates to a method of dispensing a suture secured to one end of a needle, comprising taking a device for storing and dispensing a suture and needle as described hereinbove, tearing a portion of the first panel layer away therefrom so as to expose the needle and at least a portion of the suture connected thereto, pressing down on the third panel means along the second predetermined axis such that the first panel means is flexed so as to expose the remaining portion of the needle free of the first panel means, and withdrawing the needle from the second window portion and thereafter withdrawing the suture from the inner container.

BRIEF DESCRIPTION OF THE DRAWINGS

The present invention is described in detail below herein with reference to the drawings in which:

FIG. 3 is a frontal view of inner container in an exposed and open condition.

FIG. 4 is a frontal view of the inner container of FIG. 3 illustrating a first closed position wherein the suture thread is enclosed by overlapping panels.

FIG. 5 is a frontal view of the inner container of FIG. 4 illustrating the inner container in a closed second condition ready for insertion within the outer container.

FIG. 6 is a back view of the inner container of FIG. 5.

FIG. 7 is a slightly enlarged cross-sectional view taken along the line 7—7 of FIG. 2.

FIG. 8 is a slightly enlarged cross-sectional view of the suture package of FIG. 7 illustrating the removal of the window portion of the outer layer of the first outer layer and illustrating the inner container in a dispensing condition.

BEST MODE FOR CARRYING OUT THE INVENTION

Figure 1:
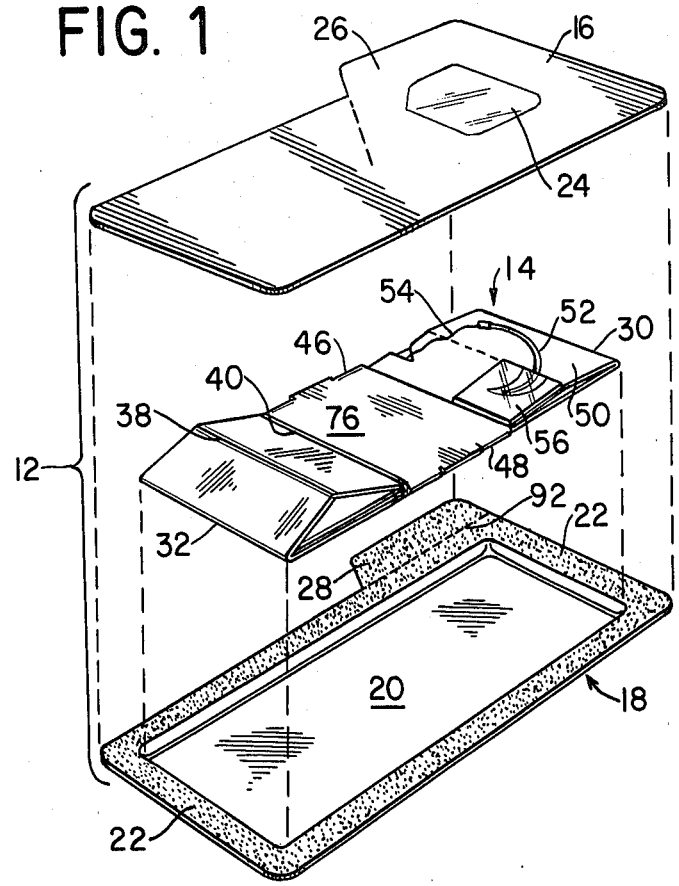
FIG. 1 is an exploded view of a suture package according to the present invention illustrating the outer and inner containers.
Figure 2:
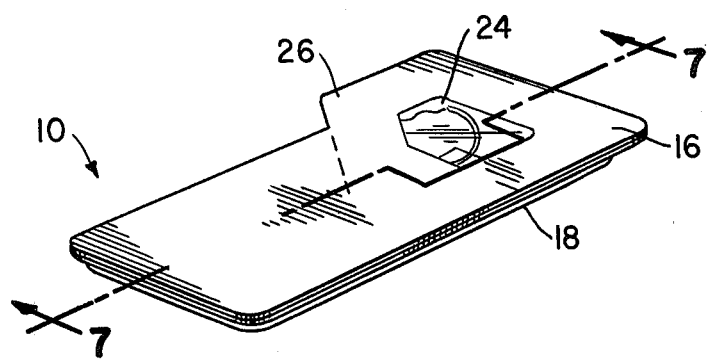
FIG. 2 is a perspective view of the suture package of FIG. 1 in a closed and sealed condition.

In the description which follows, any reference to either orientation or direction is intended primarily for the purpose of illustration and is not intended in any way as a limitation of the scope of the present invention.

Referring to the drawings, a device or suture package 10 is illustrated according to the present invention for dispensing an armed suture. As used herein, the term "armed suture" is meant to include surgical strands used for suturing, ligating and the like which includes at least one needle attached to one end of the surgical strand. Thus, the term "armed suture" includes both so-called "single" and "double" armed sutures. As more clearly illustrated in FIG. 1, the suture package 10 includes an outer container 12 and an inner container 14 which is enveloped and enclosed within the outer container 12.

The outer container 12 consists of two generally flat sheet-like panel layers 16 and 18 which are of a similar configuration and dimension. The lower panel layer 18 includes a centrally depressed region 20 which is shaped and sized to receive the inner container 14. A shoulder 22 extends all about the region 20. Preferably the sheet-like panel layers 16 and 18 are rectangular and are sealed together by suitable means known to the art along their periphery so as to define therebetween an enclosed region in which the inner container 14 is enclosed. The upper panel layer 16 includes adjacent to one end thereof a window 24 which is constructed of a transparent material so as to permit viewing of the interior region 20 of outer container 12. The first and second panel layers 16, 18 each include a tab, 26 and 28, respectively, which are similarly positioned adjacent the window portion 24. The tabs 26 and 28 permit tearing away of a portion of first panel layer 16 as will be explained in greater detail below. This in turn exposes the inner region 20 defined between the first and second layer panels 16, 18 and, accordingly, the inner container 14 located therein. Alternatively, the upper panel layer 16 can be adapted so as to permit peeling of the upper panel layer 16 away from the lower panel 18.

Preferably the first and second panel layers 16, 18 are constructed of a transparent flexible plastic material, e.g., polyethylene or other suitable plastic-like material, which is capable of receiving imprinting thereon. This permits the imprinting of numerous indicia and identifying symbols including, without limitation, identification of the type of suture, the number of sutures contained, the length and color, particularly where color aids in further identifying the type of suture, instructions or directions for use, and any other information to be directed to the user or handler. The plastic composition also permits layers to be sealed together by heat sealing methods. Alternatively, one of the panel layers may be formed of a layer of aluminum foil such as panel layer 18 which would thereby improve the barrier properties of the outer container 12. In yet still another embodiment, either or both panel layers can be formed, with allowance for the window 24 in regard to upper panel layer 16, of a series of two or more overlapping layers of different or similar types of material. For example, panel layer 18 may be composed on its outer surface of a clear transparent material, e.g., polyethylene or other suitable material, to receive if desired indicia as indicated above while also including a superimposed inner facing layer of aluminum foil.

Referring now to FIG. 3, the inner container 14 is integrally formed of a flat sheet-like material having score lines 30, 32, 34, 36, 38, 40, 42, 44, 46 and 48. An upper panel 50 is generally rectangular and is configured to receive and retain a needle 52 having a suture 54 attached to it on one end thereof. The needle is positioned between score lines 30 and 36 and across score line 34 for reasons which will be described in greater detail below. The upper panel 50 includes a window portion 56 which is shown more clearly in FIG. 1. The window portion 56 is formed of a transparent material, e.g., polyethylene, which permits viewing of the needle therethrough. The window portion 56 is secured to the surface of upper panel 50 by an adhesive 58 having a contour such that a portion of the upper surface of upper panel 40 is free of the adhesive 58 so as to form a pocket 60. The thickness of the adhesive 58 is such so as to permit the window portion 56 to retain the needle 52 in a snug or tight-fitting relationship therein. Preferably, the window portion is a clear polyfilm. Alternatively, the adhesive 58 can be replaced with a polycoating such that the window portion 56 can be selectively heat sealed to the upper panel 50. The upper panel 50 along its longitudinal edges above the score line 36 includes a pair of tabs 63 and 64 whose functions will become evident below.

The upper panel 50 is foldably secured to a center panel 62 which is also rectangular in configuration. The center panel 62 receives a major portion of the suture 54 which is placed or positioned in a predetermined arrangement upon a surface of center panel 62 as shown in FIG. 3. The arrangement of the remaining portion of the suture 54 is such as to prevent entangling or kinking of the major portion of the suture during its withdrawal from the center panel 62. Such arrangements are well known in the art, for example, a figure-eight coil as shown in FIG. 3. To assist in the process of assembling or arranging the suture 54 upon center panel 62, two apertures 65 and 66 are provided thereon through which posts (not shown) may be inserted. These posts serve on stops during the arrangement or winding of the suture 54 into the figure-eight configuration.

A pair of side panels 68 and 70 are foldably secured to the center panel 62 along score lines 42 and 44, respectively. The side panel 68 and 70 are positioned and configured such that they they may be folded along their respective score lines, 42 and 44, so as to overlap and completely enclose the remaining portion of the suture 54 positioned on the center panel 62. In this fashion, the suture 54 is securely retained in a fixed position during storage and subsequent handling. The side panel 68 and 70 include apertures 72 and 74, respectively, which overlap the aperture 65 on the center panel 62. In this fashion, the apertures 72 and 74 can be positioned over a post as noted above so as to help secure the side panels 68 and 70 during the process of assembling the inner container 14 as shown in FIG. 4.

Thereafter, the upper panel 50 is slidably folded over score line 30 onto the outermost surface of the side panels 68 and 70 as illustrated in FIG. 4. The upper panel 50 includes a notch 75 as illustrated in FIGS. 3 and 4 through which the suture 54 can pass. The notch 75 acts as a guide so as to further prevent any entangling of the suture 54 upon withdrawal from the inner container 14.

A lower panel 76 is foldably secured to the center panel 62 and is also rectangular in configuration. The lower panel 76 is slidably folded over score line 32 so as to overlap the upper most surface portion of the upper panel 50. The lower panel 76 includes a pair of side panels 78 and 80 secured to the lower panel 76 along score lines 46 and 48, respectively. Together with lower panel 76 the side panels 78 and 80 define slit-like apertures 82 and 84, respectively, which engage the tabs 63 and 64 as shown in FIGS. 5 and 6. The side panels 78 and 80 include a pair of oppositely facing curvilinear cutouts 86 and 88 as shown in FIG. 4. Upon folding of lower panel 76 along score line 32, the side panels 78 and 80 are folded along score lines 46 and 48 so as to overlap the under-surface of center panel 62. Furthermore, the side panels 78 and 80 are interlocked as shown in FIG. 6 by cooperating engagement of the curvilinear cutouts of the side panels 86 and 88.

After the inner container 10 has been assembled as shown in FIGS. 5 and 6, it assumes the configuration shown in cross-section in FIGS. 7 and 8. In particular, the length of the upper panel 50 and the lower panel 76 are such that when they are folded along score lines 30 and 32 respectively, and thereafter are coupled together as described above, at least one of the panels assumes a raised condition either about score line 34 or 38. As shown in FIG. 7, the upper panel 50 is generally flat so that the needle 52 rests upon the outer surface of upper panel 50. Simultaneously, the lower panel 76 is raised along score line 38. Upon applying pressure as shown in FIG. 8 to the score line 38, the lower panel 76 flexes about score line 34 so as to assume a generally flat configuration whereupon the upper panel 50 flexes about score line 30 so as to assume a raised configuration. Accordingly, the needle portion previously resting upon the upper panel 50 between score lines 30 and 34 is elevated or exposed free of the upper panel 50.

Preferably, the center panel 62, the upper and lower panels 50 and 76, and the side panels 68, 70, 78 and 80 are integrally constructed of a bleached sulphite board. Furthermore, the composition of the panels is such that they are capable of being sterilized by either irradiation means or by other known sterlizing methods such as employing ethylene oxide.

Upon folding of the respective panels in the fashion as illustrated in FIGS. 5 and 6, the inner container 14 is placed within depression 20 between the upper panel layer 16 and the lower panel layer 18. In loading the inner container 14 into the depression 20, it is preferred that the upper panel 50 assume a generally flat configuration. Thereafter the layers 16 and 18 are sealed together as indicated above. The inner container 14 is positioned between the layers 16, 18 such that the window 56 is positioned beneath window 24. Preferably, the window 24 is of a larger surface dimension than window 56 and is positioned with respect to window 56 so as to permit viewing of the entire needle 52 and at least a portion of the suture 54 without having to resort to opening a portion of the suture package 10. For this reason, the windows 24 and 56 preferably are constructed of a transparent material such as polyethylene.

Upon sealing of the panel layer 16 and 18 together, the complete suture package 10 is obtained as illustrated in FIG. 1 and is ready for use. After insertion and sealing of the inner container 14 between the panel layers 16, 18, the suture package 10 is sterilized by irradiation or other suitable means so that the inner container can be maintained in a sterile condition during its storage. Thereafter, the suture package 10 can be stored indefinitely with the assurance that the sterile environment between the panel layers 16 and 18 is maintained.

In use, the handler, such as a nurse or surgeon, would select a given suture package 10 in accordance with the need of the handler and the information provided on the outer surface of panel layer 16. Moreover, the window 24 as well as window 56 permits the handler to determine if the suture contained therein is of the necessary or desired type. The color of the suture 54 could provide further identification of the type of suture contained within the suture package 10. Upon selection of a desired suture package 10, the handler would then tear away a portion of the panel layer 16 by pulling on tabs 26 and 28. The tab 28 has a line of weakening 92 which permits the tab 28 to be separated together with tab 26 away from the rest of lower panel 18. The upper panel layer 16 tears by an amount determined by the length of tab 26 in a direction generally transversely across the width of the outer layer of panel 16 so as to reveal the needle 52 and a portion of suture 54.

Thereafter the suture package 10 is depressed as shown in FIG. 8 so as to flatten the lower panel 76 whereupon upper panel 50 is flexed as described above about score line 34. As a result, the needle portion extending outwardly of the pocket 60 is exposed and stands free of the upper surface of upper panel 50 together with a portion of the suture 52 as illustrated in FIG. 8. The suture package 10 need only be partially depressed in order that the aforementioned needle portion be exposed free of the upper panel 50.

In this fashion, the needle can be easily grasped with a pair of typical needle holders either by a right or left-handed handler. The dispensing of the needle and suture, therefore, is obtained from the suture package 10 in an efficient and expeditious manner.

The above-described inner container 14 is not limited as to the number of sutures 54 and corresponding needles 52 which can be retained thereby. In this regard, a series of pockets 60 can be formed under the window 56 to receive the desired number of needles 52. Accordingly, the corresponding sutures 54 are separately retained by the upper panel 50 so that any individual needle and respective suture can be withdrawn without disturbing the remaining needles and sutures.

We claim:

1. A container for dispensing at least one suture secured to one end of a needle, comprising:
   a. first panel means for retaining a portion of the needle, said first panel means capable of flexing about a first predetermined axis such that the remaining portion of the needle is exposed free of said first panel means upon flexing of said first panel means about said first predetermined axis;

b. second panel means for retaining a major portion of the suture, said second panel means being connected to said first panel means and configured such that the suture can be withdrawn therefrom upon removal of the needle from said first panel means; and c. third panel means connected to said second panel means and coupled to said first panel means, said third panel means capable of being displaced so as to effect flexing of said first panel means about said first predetermined axis, so as to expose said remaining portion of the needle free of said first panel means.

2. A container for dispensing a suture secured to one end of a needle, comprising:

a. first panel means for securely retaining a portion of the needle, said first panel means capable of flexing about a first predetermined axis in the plane of said first panel means such that the remaining portion of the needle is exposed free of said first panel means upon flexing of said first panel means about said first predetermined axis;

b. second panel means for securely retaining a major portion of the suture, said second panel means being connected to the first panel means and configured such that the suture can be withdrawn therefrom upon removal of the needle from said first panel means; and c. third panel means connected to said second panel means and coupled to said first panel means, said third panel means capable of flexing about a second predetermined axis in the plane of said third panel means such that upon flexing of said third panel means about said second predetermined axis said first panel means is also flexed about said first predetermined axis so as to expose said remaining portion of the needle free of said first panel means.

3. The container according to claim 2 wherein said first panel means includes a window portion permitting viewing of the needle retained in secured relationship with said first panel means.

4. The container according to claim 3 wherein said window portion is constructed of transparent material.

5. The container according to claim 4 wherein said first and said second panel means are of a generally rectangular configuration.

6. The container according to claim 5 wherein said first and said second panel means are foldably secured to each other along respective width edges thereof, said width edges being aligned with said first predetermined axis.

7. The container according to claim 6 further including means for enclosing the major portion of the suture retained by said second panel means.

8. The container according to claim 7 wherein said suture enclosing means includes a first pair of panels foldably secured to said second panel means along respective longitudinal edges thereof, said first pair of panels capable of being folded over onto said second panel means such that the major portion of the suture is substantially enclosed.

9. The container according to claim 8 wherein said first panel means is folded over along its longitudinal edge connected to said first panel means so as to slidably overlap a surface portion of said first pair of panels in their folded condition enclosing the major portion of the suture.

10. The container according to claim 9 wherein said third panel means is of a generally rectangular configuration.

11. The container according to claim 10 wherein the other width edge of said second panel means is foldably secured to a width edge of said third panel means, said width edges being aligned with said second predetermined axis.

12. The container according to claim 11 further including means for coupling said first panel means and said third panel means.

13. The container according to claim 12 wherein said coupling means includes a second pair of panels each foldably secured to a respective longitudinal edge of said third panel means.

14. The container according to claim 13 wherein said third panel means is folded over along its longitudinal edge connected to said second panel means so as to slidably overlap a surface portion of said first pair of panels in their folded condition enclosing the major portion of the suture.

15. The container according to claim 14 further including an aperture positioned adjacent a longitudinal edge of of said first panel means, said aperture capable of guiding the major portion of the suture during its withdrawal from said second panel means.

16. The container according to claim 15 wherein said second panel means includes means for maintaining the major portion of the suture in a predetermined configuration so as to prevent entangling or kinking of the major portion of the suture during dispensing of the suture therefrom.

17. The container according to claim 13 wherein each of said panel means and each of said pairs of panels are integrally constructed of a bleached sulphite board.

18. The container according to claim 17 wherein each of said panel means and each of said pairs of panels are capable of being sterilized by at least one of irradition and ethylene oxide sterilizing methods.

19. A device for storing and dispensing a suture secured to one end of a needle, comprising:

a. outer container means including a first panel layer and a second panel layer of generally like configuration and dimension, said first and second panel layers being secured together along their peripheries so as to define an enclosed region therebetween, said first panel layer including a first window portion permitting viewing of said enclosed region;

b. inner container means positioned within said region including:

(1) first panel means for securely retaining a portion of the needle, said first panel means capable of flexing about a first predetermined axis in the plane of said first panel means such that the remaining portion of the needle is exposed free of said first panel means upon flexing of said first panel means about said first predetermined axis, said first panel means including a second window portion permitting viewing of the needle retained in secured relationship with said first panel means;

(2) second panel means for securely retaining a major portion of the suture, said second panel means being connected to the first panel means and configured such that the suture can be withdrawn therefrom upon removal of the needle from said first panel means; and (3) third panel means connected to said second panel means and coupled to said first panel means, said third panel means capable of flexing about a second predetermined axis in the plane of said third panel means such that upon flexing of said third panel means about said second predetermined axis, said first panel means is also flexed about said first predetermined axis so as to expose said remaining portion of the needle free of said first panel means.

20. The device according to claim 19 wherein said first window portion is of a larger surface dimension than said second window portion.

21. The device according to claim 20 wherein said first window portion overlies said second window portion such that the entire needle together with at least a portion of the suture can be viewed through said first and said second window portions.

22. The device according to claim 21 wherein said first and said second window portions are constructed of transparent material.

23. The device according to claim 22 wherein said first panel layer includes a tab adjacent said first window so as to permit tearing and removal of a portion of said first panel layer adjacent the needle.

24. The device according to claim 23 wherein said first and said second panel layers are each of a generally rectangular configuration.

25. The device according to claim 24 wherein said first and said second panel layers are constructed of a clear polyester capable of being imprinted so as to provide numerical and identifying indicia thereon.

26. The device according to claim 25 further including a layer of metallic foil superimposed on at least one surface of said second panel layer.

27. The device according to claim 26 wherein said first and said second panel layers are capable of being sterilized by at least one of irradiation and ethylene oxide sterilizing methods.

28. The device according to claim 19 wherein said inner container is of a generally rectangular configuration and is configured and dimensioned so as to be capable of being enclosed within said region defined between said first and said second panel layers.

29. The container according to claim 28 wherein said first and said second panel means are foldably secured to each other along respective width edges thereof, said width edges being aligned with said first predetermined axis.

30. The container according to claim 29 further including means for enclosing the major portion of the suture retained by said second panel means.

31. The container according to claim 30 wherein said suture enclosing means includes a first pair of panels foldably secured to said second panel means along respective longitudinal edges thereof, said first pair of panels capable of being folded over onto said second panel means such that the major portion of the suture is substantially enclosed.

32. The container according to claim 31 wherein said first panel means is folded over along its longitudinal edge connected to said first panel means so as to slidably overlap a surface portion of said first pair of panels in their folded condition enclosing the major portion of the suture.

33. The container according to claim 32 wherein said third panel means is of a generally rectangular configuration.

34. The container according to claim 33 wherein the other width edge of said second panel means is foldably secured to a width edge of said third panel means, said width edges being aligned with said second predetermined axis.

35. The container according to claim 34 further including means for coupling said first panel means and said third panel means.

36. The container according to claim 35 wherein said coupling means includes a second pair of panels each foldably secured to a respective longitudinal edge of said third panel means.

37. The container according to claim 36 wherein said third panel means is folded over along its longitudinal edge connected to said second panel means so as to slidably overlap a surface portion of said first pair of panels in their folded condition enclosing the major portion of the suture.

38. The container according to claim 37 further including an aperture positioned adjacent a longitudinal edge of of said first panel means, said aperture capable of guiding the major portion of the suture during its withdrawal from said second panel means.

39. The container according to claim 38 wherein said second panel means includes means for maintaining the major portion of the suture in a predetermined configuration so as to prevent entangling or kinking of the major portion of the suture during dispensing of the suture therefrom.

40. The container according to claim 1 wherein each of said panel means and each of said pairs of panels are integrally constructed of a bleached sulphite board.

41. The container according to claim 40 wherein each of said panel means and each of said pairs of panels are capable of being sterilized by at least one of irradiation and ethylene oxide sterilizing methods.

42. A method of dispensing a suture secured to one end of a needle, comprising:
a. taking a device for storing and dispensing a suture and needle, said device including:
   (1) outer container means including a first panel layer and a second panel layer of generally like configuration and dimension, said first and second panel layers being secured together along their peripheries so as to define an enclosed region therebetween, said first panel layer including a first window portion permitting viewing of said enclosed region;
   (2) inner container means positioned within said region including:
      (a) first panel means for securely retaining a portion of the needle, said first panel means capable of flexing about a first predetermined axis in the plane of said first panel means such that the remaining portion of the needle is exposed free of said first panel means upon flexing of said first panel means about said first predetermined axis, said first panel means including a second window portion permitting viewing of the needle retained in secured relationship with said first panel means;
      (b) second panel means for securely retaining a major portion of the suture, said second panel means being connected to the first panel means and configured such that the suture can be withdrawn therefrom upon removal of the needle from said first panel means; and (c) third panel means connected to said second panel means and coupled to said first panel means, said third panel means capable of flexing about a second predetermined axis in the plane of said third panel means such that upon flexing of said third panel means about said second predetermined axis, said first panel means is also flexed about said first predetermined axis so as to expose said remaining portion of the needle free of said first panel means;

b. tearing a portion of said first panel layer away therefrom so as to expose said needle and at least a portion of the suture connected thereto;

c. pressing down on said third panel means along said second predetermined axis such that said first panel means is flexed so as to expose said remaining portion of the needle free of said first panel means; and d. withdrawing the needle from said second window portion and thereafter withdrawing the suture from said inner container.

* * * * *